United States Patent
Chen et al.

(10) Patent No.: US 6,288,230 B1
(45) Date of Patent: Sep. 11, 2001

(54) 2-(2, 3-DIHYDROBENZOFURAN-5-YL)-4-AMINOMETHYLIMIDAZOLES: DOPAMINE RECEPTOR SUBTYPE SPECIFIC LIGANDS

(75) Inventors: Xi Chen, Killingworth; Xiao-shu He, Branford, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/408,035

(22) Filed: Sep. 29, 1999

Related U.S. Application Data

(60) Provisional application No. 60/102,258, filed on Sep. 29, 1998.

(51) Int. Cl.[7] ........................ C07D 241/02; C07D 405/00; C07D 403/00; C07D 233/54; C07D 317/08
(52) U.S. Cl. .................. 544/295; 544/242; 546/196; 546/210; 548/300.1; 548/311.1; 548/312.4; 549/229; 549/356; 549/398
(58) Field of Search .................... 544/242, 295; 546/196, 210; 548/300.1, 311.1, 312.4; 549/229, 356, 398

(56) References Cited

U.S. PATENT DOCUMENTS

| | | | |
|---|---|---|---|
| 3,786,061 | 1/1974 | Novello et al. | 260/296 |
| 3,818,014 | 6/1974 | Baldwin et al. | 260/288 |
| 4,032,522 | 6/1977 | Baldwin et al. | 260/250 |
| 4,125,530 | 11/1978 | Baldwin et al. | 546/167 |
| 5,159,083 | 10/1992 | Thurkauf et al. | 548/335.5 |
| 5,428,164 | 6/1995 | Thurkauf et al. | 544/295 |
| 5,478,934 | 12/1995 | Yuan et al. | 540/546 |
| 5,633,376 | 5/1997 | Thurkauf et al. | 544/360 |
| 5,633,377 | 5/1997 | Thurkauf et al. | 544/370 |
| 5,646,279 | 7/1997 | Thurkauf et al. | 544/295 |
| 5,646,280 | 7/1997 | Thurkauf et al. | 544/295 |
| 5,646,281 | 7/1997 | Thurkauf et al. | 544/295 |
| 5,654,762 | 8/1997 | Thurkauf et al. | 544/370 |
| 5,681,956 | 10/1997 | Thurkauf et al. | 544/295 |
| 5,712,392 | 1/1998 | Thurkauf et al. | 544/295 |
| 5,750,700 | 5/1998 | Yuan et al. | 546/148 |
| 5,760,234 | 6/1998 | Yuan et al. | 546/208 |
| 5,905,152 | 5/1999 | Gala et al. | 544/295 |
| 6,002,005 | 12/1999 | Yuan et al. | 544/358 |

FOREIGN PATENT DOCUMENTS

| | | |
|---|---|---|
| 20 61 515 | 6/1971 | (DE) . |
| WO 92/12134 | 7/1992 | (WO) . |
| WO 96/10018 | 4/1996 | (WO) . |
| WO 96/16040 | 5/1996 | (WO) . |
| WO 96/16057 | 5/1996 | (WO) . |
| WO 97/43279 | 11/1997 | (WO) . |

OTHER PUBLICATIONS

Bradsher et al., *J. Org. Chem.*, 46: 1384–1388, (1981), "Oxygen Heterocycles by the Parham Cyclialkylation."

Andrews, C.H., et al., "Experimental chemotherapy of typhus Anti-rickettsial action of p-sulphonamidobenzamidine and related compounds," *National Institute for Medical Research*, Hampstead, Dec. 1944, pp. 20–62.

Bartfield, et al., "Conformational, Bond-Order, and Substituent Dependencies of Orthobenzylic Coupling Constants," *Dept. of Chemistry*, et al., Aug. 1982, pp. 2178–2186.

Liégeois, et al., "Dopamine $D_4$ Receptors: A New Opportunity for Research on Schizophrenia,"*Current Medical Chemistry*, 1998, 5., pp. 77–100.

Matsumura, et al., "Studies ofNitriles. XI.[1)] Preparation and Chemistry ofSchiff Bases of ADAN, 2–Amino–3, 3–dichloroacrylonitrile.[2)] A highly Effective Conversion into 2–Substituted–4(5)–chloroimidazole–5(4)–carbaldehydes," *Chemical Research Laboratories*, 1976, vol. 24, pp. 960–969.

Thurkauf, et al., "2–Phenyl–4(5)–[[4–(pyrimidin–2–yl) piperazin–1–yl] methyl]imidazole. A Highly Selective Antagonist at Cloned Human $D_4$ Receptors," *Journal of Medicinal Chemistry*, vol. 40 No. 1, pp. 1–3.

Thurkauf, et al., "2–Phenyl–4–(aminomethyl)imidazoles as Potential Antipsychotic Agents. Synthesis and Dopamine $D_2$ Receptor Binding," *J. Med.Chem.* 1995, 38, pp. 2251–2255.

*Primary Examiner*—Bruck Kifle
*Assistant Examiner*—Sudhaker B. Patel
(74) *Attorney, Agent, or Firm*—McDonnell Boehnen Hulbert & Berghoff; Steven J. Sarussi

(57) ABSTRACT

Disclosed are compounds of the formula:

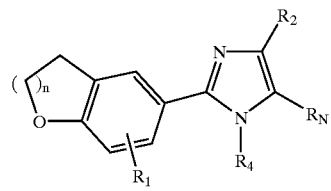

or the pharmaceutically acceptable acid addition salts thereof wherein:

n is an integer;

$R_1$ represents an organic or inorganic group;

$R_2$ represents halogen or $C_1$–$C_6$ alkyl;

$R_N$ is an alkylene carrying a substituted piperazine, piperidine, or tetrahydropyridine; and $R_4$ is hydrogen or $C_1$–$C_6$ alkyl, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

35 Claims, No Drawings

2-(2, 3-DIHYDROBENZOFURAN-5-YL)-4-AMINOMETHYLIMIDAZOLES: DOPAMINE RECEPTOR SUBTYPE SPECIFIC LIGANDS

This is a provisional of application Ser. No. 60/102,258, filed Sep. 29 1998.

BACKGROUND OF THE INVENTION

1. Field of the Invention

This invention relates to 2-(2,3-dihydrobenzofuran-5-yl)-4-aminomethylimidazoles and to pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 350: 610 (Van Tol et al., 1991); Nature, 347: 146 (Sokoloff et al., 1990)). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

U.S. Pat. No. 5,428,164 describes phenylimidazole derivatives.

SUMMARY OF THE INVENTION

This invention provides novel compounds of Formula I which interact with dopamine subtypes. Accordingly, a broad embodiment of the invention is directed to a compound of Formula I:

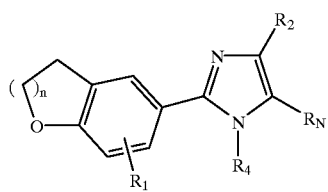

or pharmaceutically acceptable acid addition salts thereof wherein:

n is 1, 2, or 3;

$R_1$ represents hydrogen, halogen, $C_1$–$C_6$ alkyl, $C_1$–$C_6$ alkoxy, $C_1$–$C_6$ alkylthio, hydroxy, amino, mono- or di($C_1$–$C_6$)alkylamino, cyano, nitro, trifluoromethyl or trifluoromethoxy;

$R_2$ represents halogen or $C_1$–$C_6$ alkyl;

$R_N$ is

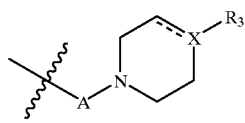

where

A is alkylene of 1 to 4 carbon atoms;

X is either a carbon atom, CH, or nitrogen; and $R_3$ represents either an (un)substituted aryl or a heteroaryl group; and $R_4$ is hydrogen or $C_1$–$C_6$ alkyl.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In another aspect, the invention provides intermediates useful in the preparation of compounds of Formula I.

DETAILED DESCRIPTION OF THE INVENTION

As mentioned above, the invention encompasses aminomethylimidazole derivatives of Formula I. Preferred com pounds of Formula I are those where n is 1 and are represented by Formula IA.

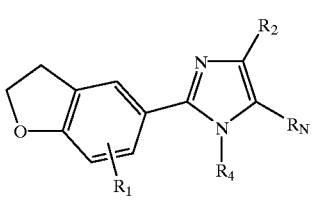

where $R_1$, $R_2$, $R_4$, and $R_N$ are as defined above for Formula I.

Suitable $R_3$ groups include aryl and heteroaryl groups optionally substituted with up to three groups independently selected from halogen, $C_1$–$C_6$ alkyl, $C_1$–$C_6$ alkoxy, hydroxy, phenyl, amino, mono- or di($C_1$–$C_6$)alkylamino, and perfluoroalkyl, such as trifluoromethyl. Other substituents include lower, i.e. $C_1$–$C_6$, alkylthio, $C_1$–$C_6$ acyloxy, aryl, and heteroaryl. These latter aryl and heteroaryl substituents may also be substituted in a fashion similar to the parent aryl or heteroaryl group.

Representative aryl groups are aromatic carbocyclic groups having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl).

Representative heteroaryl groups (aromatic heterocycles) include groups having one or more aromatic ring systems of 5, 6, or 7 members, preferably 5 or 6 members, containing at least one and up to four hetero atoms, preferably one or two hetero atoms, selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl.

The hetero aryl $R_3$ groups are bound to the parent piperazine, piperidine or tetrahydropyridine group via a carbon atom in the hetero aryl group, preferably a carbon atom immediately adjacent a hetero atom such as nitrogen in the hetero aryl group.

Preferred compounds of Formula IA are those where X is nitrogen and $R_3$ is pyrimidinyl, phenyl, pyridyl, naphthyl, benzyl, 4,5-benzopyrimidin-2-yl, or isoquinolinyl, preferably 1-isoquinolinyl, each of which $R_3$ groups is optionally unsubstituted or substituted with up to three groups selected from halogen, $C_1$–$C_6$ alkyl, $C_1$–$C_4$ alkoxy, hydroxy, phenyl, amino, mono- or di($C_1$–$C_6$)alkylamino, or trifluoromethyl.

Other preferred compounds of Formula IA are those where X is carbon or CH and $R_3$ is pyrimidinyl, phenyl, pyridyl, naphthyl, benzyl, benzopyrimidin-yl, or isoquinolinyl, preferably 1-isoquinolinyl, each of which $R_3$ group is optionally unsubstituted or substituted with up to three groups selected from halogen, $C_1$–$C_6$ alkyl, $C_1$–$C_4$ alkoxy, hydroxy, phenyl, amino, mono- or di($C_1$–$C_6$)alkylamino, or trifluoromethyl.

More preferred compounds of Formula IA are those where A is methylene, $R_3$ is phenyl, 2-pyridyl, pyrimidin-2-yl, 1-or 2-naphthyl, quinolinyl, preferably 2-quinolinyl, isoquinolinyl, preferably 1-isoquinolinyl, 4,5-benzopyrimidin-2-yl or benzoisothiazol-3-yl, each of which is optionally substituted with up to three groups selected from halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, phenyl, nitro, trifluoromethyl or trifluoromethoxy.

Thus, the invention encompasses compounds of Formula II:

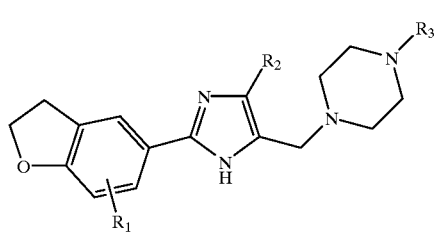

where $R_1$, $R_2$, and $R_3$ are as defined above for Formula I.

Preferred compounds of Formula II include those where $R_3$ is phenyl, pyridyl, more preferably 2-pyridyl, pyrimidin-2-yl, 1 or 2 naphthyl, quinolinyl, isoquinolinyl, preferably 1-isoquinolinyl, benzopyrimidinyl or benzoisothiazol-3-yl, each of which is optionally substituted with up to three groups selected from halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, phenyl, trifluoromethyl or trifluoromethoxy.

More preferred compounds of Formula II include those where $R_3$ is a pyrimidinyl group optionally substituted with up to three groups selected from $C_1$–$C_6$ alkyl, trifluoromethyl, halogen, or phenyl.

Other more preferred compounds of Formula II are those where $R_3$ is phenyl optionally substituted with up to three groups selected independently from $C_1$–$C_6$ alkoxy, $C_1$–$C_6$ alkyl, halogen, trifluoromethyl, and phenyl.

Particularly preferred compounds of Formula II where $R_3$ is phenyl include those where the phenyl group is mono- or disubstituted independently with $C_1$–$C_6$ alkoxy, $C_1$–$C_6$ alkyl, chloro, fluoro, and trifluoromethyl.

The invention also encompasses compounds of Formula III.

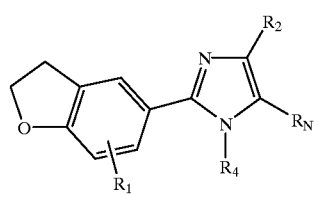

$R_1$, $R_4$ and $R_2$ are as defined above for Formula I; and $R_N$ is

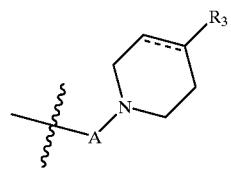

where

A is alkylene of 1 to 2 carbon atoms; and
$R_3$ is as defined above for Formula I.

Preferred compounds of Formula III include those where $R_N$ is

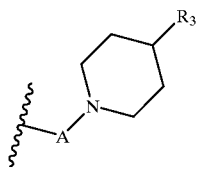

where $R_3$ is as defined above for Formula I.

Such compounds are hereinafter referred to as compounds of Formula III-A. Preferred compounds of III-A include those where $R_4$ is hydrogen, $R_3$ is phenyl, benzyl, 2-pyridyl, or pyrimidin-2-yl. Particularly preferred compounds of Formula III-A are those where $R_4$ is hydrogen, $R_3$ is phenyl or benzyl optionally substituted with one to three groups independently selected from halogen, hydroxy, $C_1$–$C_6$ alkyl, $C_1$–$C_6$ alkoxy, amino, or mono- or di($C_1$–$C_6$)alkylamino.

Other preferred compounds of Formula III include those where $R_N$ is

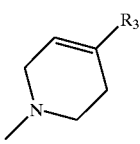

where $R_3$ is as defined above for Formula I.

Such compounds are hereinafter referred to as compounds of Formula III-B. More preferred compounds of III-B include those where $R_4$ is hydrogen, $R_3$ is phenyl, benzyl, 2-pyridyl, or 2-pyrimidinyl. Particularly preferred compounds of Formula III-B are those where $R_3$ is phenyl or benzyl optionally substituted with one to three groups independently selected from halogen, hydroxy, $C_1$–$C_6$ alkyl, $C_1$–$C_6$ alkoxy, amino, or mono- or di($C_1$–$C_6$)alkylamino.

The invention also provides intermediates useful in preparing compounds of Formula I. These intermediates have Formulae IV-A, IV-B, and IV-C.

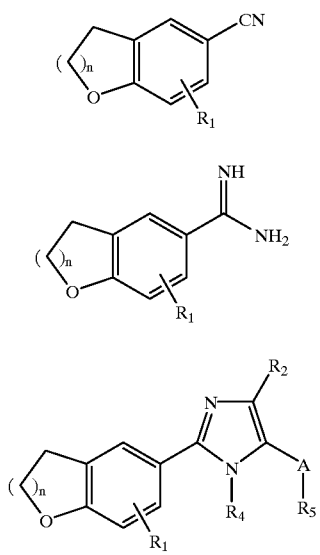

In each of Formulae IV-A-C, A, n, $R_1$ and $R_2$ are as defined above for Formula I. In Formula IV-C, $R_4$ is as defined above for Formula I, and $R_5$ is hydroxy or halogen. Preferred compounds of Formulae IV-A-C are those where n is 1. Preferred halogens at $R_5$ in IV-C are chloro and fluoro. Particularly preferred compounds of Formulae IV-A-C, are those where $R_1$, and $R_4$ are both hydrogen.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC$—$(CH_2)_n$—$COOH$ where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Where a substituent is a di($C_1$–$C_6$)alkylamino group, the two alkyl groups are the same or different. Representative di($C_1$–$C_6$)alkylamino groups include dimethylamino, methylpropylamino, diisopropylamino, and ethylpentylamino.

Preferred aryl and heteroaryl groups are phenyl, pyridyl, pyrimidin-2-yl, 1 or 2 naphthyl, quinolinyl, isoquinolinyl, benzopyrimidinyl and benzoisothiazol-3-yl. Each of these groups may be substituted with up to three substituents which are the same or different and are selected from halogen, $C_1$–$C_6$ alkyl, $C_1$–$C_4$ alkoxy, $C_1$–$C_4$ alkylthio, hydroxy, amino, mono- or di($C_1$–$C_6$)alkylamino, cyano, nitro, trifluoromethyl and trifluoromethoxy.

Representative compounds of the invention are shown in Table 1.

TABLE 1

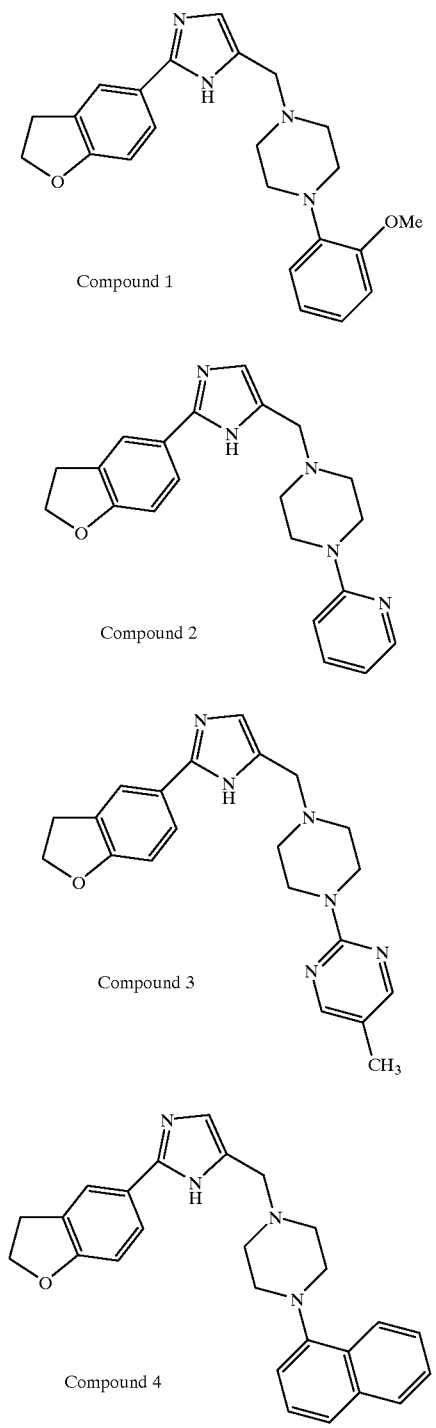

Compound 1

Compound 2

Compound 3

Compound 4

TABLE 1-continued

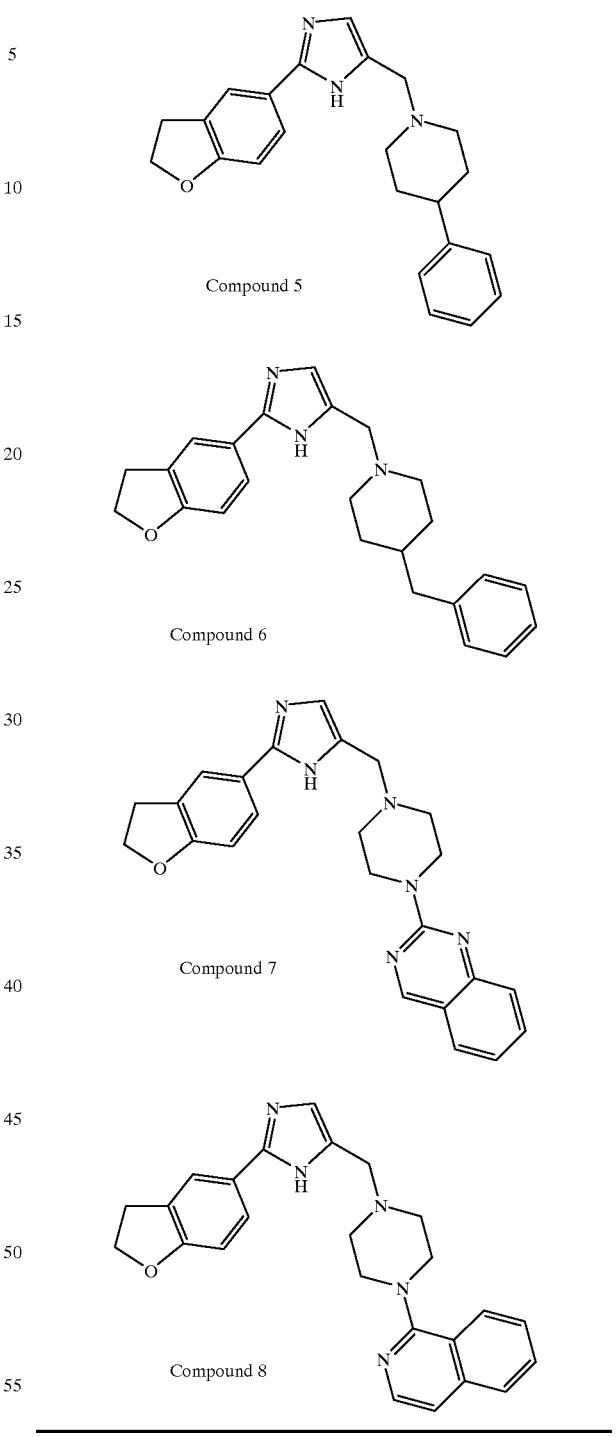

Compound 5

Compound 6

Compound 7

Compound 8

The invention also pertains to the use of compounds of general Formula I in the treatment of neuropsychological disorders. The interaction of compounds of the invention with dopamine receptors is shown in the examples. This interaction results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the compounds of the invention where n is 1 is presented in Scheme I. Those having skill in the art will recognize that the starting materials may be varied and additional steps employed to produce other compounds encompassed by the present invention.

Where they are not commercially available, the compounds of Formula V may be prepared by procedures analogous to those described in literature. The secondary amines that are employed in the synthesis of compounds of Formula I are either known or capable of being prepared by literature methods. A variety of methodologies exist for synthesizing aryl and heteroaryl substituted piperidines and piperazines. Of course, the preparation of certain secondary amines will require protection of the secondary nitrogen that is reacted with the halomethyl functionality on the imidazole ring.

Those having skill in the art will recognize that the starting material may be varied and additional steps Scheme I

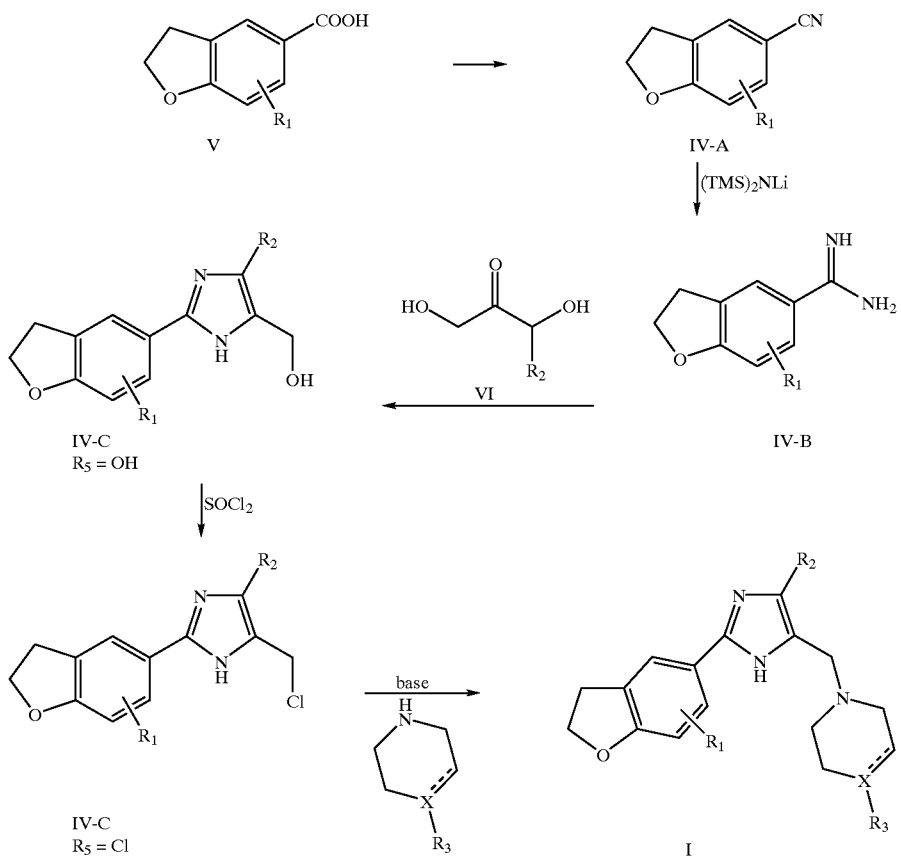

wherein $R_1$, $R_2$, $R_3$ and X are as defined above for Formula I.

As shown, a 2,3-dihydrobenzofuran-5-carboxylic acid of Formula V may be converted into corresponding 2,3-dihydrobenzofuran-5-nitrile of Formula IV-A via standard methods. Nitrile IV-A can be converted into benzamidine Formula IV-B by, for example, treatment with lithium hexamethyldisilazane in diethyl ether or, alternatively, by dissolution in a saturated solution of hydrogen chloride in methanol followed by treatment of the intermediate iminoether with ammonia. Reaction of benzamidine IV-B with an appropriately substituted dihydroxyacetone VI provides 2-(2, 3-dihydrobenzofuran-5-yl)-4-hydroxymethylimidazole IV-C ($R_5$=OH). Subsequent treatment with thionyl chloride followed by reaction with an appropriate secondary amine, generally a piperazine, piperidine or tetrahydropyridine, provides the desired compound of Formula I.

employed to produce compounds encompassed by the present invention.

The disclosures of all articles and references mentioned in this application, including patents, are incorporated herein by reference.

The preparation of the compounds of the present invention is illustrated further by the following examples which are not to be construed as limiting the invention in scope or spirit to the specific procedures and compounds described in them.

EXAMPLE 1

Preparation of Intermediates 2, 3-dihydrobenzofuran-5-nitrile

A solution of 23.6 g of 2, 3-dihydrobenzofuran-5-carboxylic acid (See: Bradsher, et al. *J. Org. Chem.*, 46, 1384 (1981)) in thionyl chloride (100 mL) is refluxed for 5 hours. After cooling to room temperature, the excess thionyl chloride is evaporated in vacuo on a rotary evaporator. The resulting residue is dissolved in chloroform (50 mL) and reconcentrated. The concentrate is dissolved in chloroform (100 mL) and ammonia gas introduced to the resulting solution until it turns basic (pH >12). The resulting mixture is then filtered through celite and the filtrate concentrated to provide an amide as a yellow solid (13.5 g). Recrystallization from ethyl acetae provides yellow crystals (9.26 g). The amide is dissolved in thionyl chloride (100 mL) and refluxed overnight. After cooling, the excess thionyl chloride is moved on a rotary evaporator. The resulting residue is taken up in diethyl ether, filtered through celite and the solvent removed under reduced pressure to give an orange solid. The solid is recrystallized from isopropanol/hexanes to give the desired nitrile as yellow crystals (7.14 g).

2.3-dihydrobenzofuran-5-amidine

A solution of 2, 3-dibenzofuran-5-nitrile (7 g, 0.0483 mol) in 300 mL of dry diethyl ether is treated with solid lithium hexamethyldisilazane (32.4 g, 0.192 mol) and the resulting mixture is stirred at room temperature overnight, and then poured into 300 mL of cold 10% HCl solution. The acidic layer is washed twice with ether, basified with 50% NaOH solution and extracted with chloroform. The chloroform extracts are dried ($Na_2SO_4$) and concentrated to give a brown oil which slowly crystallizes upon standing. Recrystallization from acetone yields 5.2 g of gray crystals.

2-(2,3-dihydrobenzofuran-5-yl)-4-hydroxymethylimidazole

A heterogeneous mixture of the amidinolpropanol immediately above (3.1 g, 20 mmol), ammonium chloride (1.0 g) and dihydroxy acetone dimer (3.5 g, 2 molar equiv) in 80 ml of conc. $NH_4OH$ is heated at reflux for about 90 minutes cooled and filtered (2.2 g, 51 %). The filtrate is used as is. Alternatively, the filtrate may be recrystallized using, e.g., ethyl acetate.

EXAMPLE 2

5-(5-{[4-(5-methylpyrimidin-2-yl)piperazinyl]-methyl}imidazol-2-yl)-2,3-dihydrobenzo[b]furan A solution of 2-(2,3-dihydrobenzofuran-5-yl)-4-hydroxymethylimidazole (500 mg, 2.3 mmol) is refluxed briefly in thionyl chloride (5 ml) and concentrated. The resultant oil (IV-C, $R_1$=H, $R_5$=Cl) is dissolved in chloroform (10 ml) and added to a solution of 1-(5-methylpyrimidin-2-yl)piperazine (0.39 g) in chloroform (10 ml) containing triethylamine (1.0 ml). After 20 minutes the solution is washed with 10% NaOH solution, dried ($Na_2SO_4$) and concentrated to afford the title compound (Compound 3) as an oil. The oil was dissolved in absolute ethanol and treated with 48% HBr until acidic. After 2 hr, the crystalline hydrobromide salt (Compound 3a) was collected by filtration (0.71 g, 59%, m. p. 241–245° C.).

EXAMPLE 3

The following compounds are prepared essentially according to the procedures set forth above in Example 1.

(a) 2-(2, 3-Dihydrobenzofuran-5-yl)-4-(1-[4-{2-methoxyphenyl}piperazin-1-yl]methyl)imidazole (Compound 1) [alternatively named 1-{4-[(2-(2,3-dihydrobenzo[b]furan-5-yl) imidazol-5-yl)methyl] piperazinyl}-2-methoxybenzene].

(b) 2-(2, 3-Dihydrobenzofuran-5-yl)-4-(1-[4-{pyridin-2-yl}piperazin-1-yl]methyl)imidazole (Compound 2)[alternatively named 5-{5-[(4-(2-pyridyl)piperazinyl) methyl]imidazol-2-yl}-2,3-dihydrobenzo[b]furan].

(c) 2-(2, 3-Dihydrobenzofuran-5-yl)-4-(1-[4-{2-napthyl}piperazin-1-yl]methyl)imidazole (Compound 4, m.p. 126–128° C.) [alternatively named 5-{5-[(4-naphthylpiperazinyl) methyl]imidazol-2-yl}-2,3-dihydrobenzo [b]furan].

(d) 2-(2, 3-Dihydrobenzofuran-5-yl)-4-(1-[4-phenylpiperidin-1-yl]methyl)imidazole hydrobromide (Compound 5).

(e) 2-(2, 3-Dihydrobenzofuran-5-yl)-4-(1-[4-benzylpiperidin-1-yl]methyl)imidazole hydrochloride, (Compound 6, m.p. 248–251° C.).

(f) 2-(2, 3-Dihydrobenzofuran-5-yl)-4-(1-[4-{4,5-benzopyrimidin-2-yl}piperazin-1-yl]methyl)imidazole hydrochloride (Compound 7, m.p. 228–230° C.).

(g) 2-(2, 3-Dihydrobenzofuran-5-yl)-4-(1-[4-{isoquinolin-1-yl}piperazin-1-yl]methyl)imidazole (Compound 8, m.p. 130–133° C.).

(h) 2-(2, 3-Dihydrobenzofuran-5-yl)-4-(1-[4-phenylpiperazin-1-yl]methyl)imidazole hydrobromide (m.p. 225–230° C.) (Compound 9).

(i) 2-(2, 3-Dihydrobenzofuran-5-yl)-4-(1-[4-{2-ethoxyphenyl}piperazin-1-yl]methyl)imidazole hydrochloride (Compound 10, m.p. 238–240° C.).

(j) 2-(2, 3-Dihydrobenzofuran-5-yl)-4-(1-[4-{2-methylphenyl}piperazin-1-yl]methyl)imidazole hydrobromide (Compound 11, m.p. 249–251° C.).

(k) 2-(2, 3-Dihydrobenzofuran-5-yl)-4-(1-[4-{3-chlorophenyl}piperazin-1-yl]methyl)imidazole (Compound 12, m.p. 100–101° C.).

(l) 2-(2, 3-Dihydrobenzofuran-5-yl)-4-(1-[4-{4-methoxyphenyl}piperazin-1-yl]methyl)imidazole hydrobromide (Compound 13, m.p. 195–200° C.).

(m) 2-(2, 3-Dihydrobenzofuran-5-yl)-4-(1-[4-{4-fluorophenyl}piperazin-1-yl]methyl)imidazole hydrobromide (Compound 14, m.p. 203–206° C.).

(n) 2-(2, 3-Dihydrobenzofuran-5-yl)-4-(1-[4-{2-fluorophenyl}piperazin-1-yl]methyl)imidazole hydrobromide (Compound 15, m.p. 250–252° C.).

(o) 2-(2, 3-Dihydrobenzofuran-5-yl)-4-(1-[4-{2-chlorophenyl}piperazin-1-yl]methyl)imidazole hydrobromide(Compound 16, m.p. 249–251° C.).

(p) 2-(2, 3-Dihydrobenzofuran-5-yl)-4-(1-[4-{3-trifluoromethylphenyl}piperazin-1-yl]methyl)imidazole hydrobromide (Compound 17).

(q) 2-(2, 3-Dihydrobenzofuran-5-yl)-4-(1-[4-{3-dimethylphenyl}piperazin-1-yl]methyl)imidazole hydrobromide (Compound 18, m.p. 264–266° C.).

(r) 2-(2, 3-Dihydrobenzofuran-5-yl)-4-(1-[4-{5-methoxypyrimidin-2-yl}piperazin-1-yl]methyl)imidazole hydrobromide (Compound 19).

(s) 2-(2, 3-Dihydrobenzofuran-5-yl)-4-(1-[4-{5-fluoropyrimidin-2-yl}piperazin-1-yl]methyl)imidazole hydrobromide (Compound 20, m.p. 250–252° C.).

(t) 2-(2, 3-Dihydrobenzofuran-5-yl)-4-(1-[4-{pyrimidin-2-yl}piperazin-1-yl]methyl)imidazole hydrochloride (Compound 21).

(u) 2-(2, 3-Dihydrobenzofuran-5-yl)-4-(1-[4-{5-phenylpyrimidin-2-yl}piperazin-1-yl]methyl)imidazole (Compound 22).

(v) 2-(2, 3-Dihydrobenzofuran-5-yl)-4-(1-[4-{4-methylpyrimidolzin-2-yl}piperazin-1-yl]methyl)imidazole hydrochloride (Compound 23, m.p. 215–218° C.).

(w) 2-(2, 3-Dihydrobenzofuran-5-yl)-4-(1-[4-{4-trifluoromethylpyrimidin-2-yl}piperazin-1-yl]methyl) imidazole hydrobromide (Compound 24, m.p. 204–210° C. dec).

(x) 2-(2, 3-Dihydrobenzofuran-5-yl)-4-(1-[4-phenyl -1,2, 5,6-tetrahydopyridin-1-yl]methyl)imidazole (Compound 25).

EXAMPLE 4

Assay For $D_2$ And $D_4$ Receptor Binding Activity

Pellets of COS cells containing recombinantly produced $D_2$ or $D_4$ receptors from African Green monkey are used for the assays. The sample is homogenized in 100 volumes (w/vol) of 0.05 M Tris HCl buffer at 40° C. and pH 7.4. The sample is then centrifuged at 30,000×g and resuspended and rehomogenized. The sample is then centrifuged again at 30,000×g and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding is defined as that binding found in the presence of 1 mM spiperone; without further additions, nonspecific binding is less than 20% of total binding. The binding characteristics of representative compounds of the invention for the $D_2$ and $D_4$ receptor subtypes are shown in Table 2.

TABLE 2

| Compound Number | $D_4$ $K_i$ (nM) | $D_2$ $K_i$ (nM) |
|---|---|---|
| 1 | 3 | 143 |
| 3a | 15 | 716 |
| 6 | 3 | 650 |
| 7 | 32 | 1128 |
| 8 | 1 | 125 |

The binding constants of compounds of Formula I for the $D_4$ receptor, expressed in nM, generally range from about 0.1 nanomolar (nM) to about 75 nanomolar (nM). These compounds typically have binding constants for the $D_2$ receptor of at least about 100 nM. Thus, the compounds of the invention are generally at least about 10 time more selective for the $D_4$ receptor than the $D_2$ receptor. Preferably, these compounds are at least 20, and more preferably at least 25–50, times more selective for the $D_4$ receptor than the $D_2$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:
1. A compound of the formula:

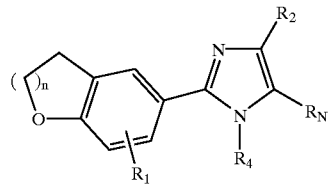

or a pharmaceutically acceptable acid addition salt thereof wherein:
n is 1, 2, or 3;
$R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, trifluoromethyl or trifluoromethoxy;
$R_2$ represents halogen or $C_1$–$C_6$ alkyl;
$R_N$ is

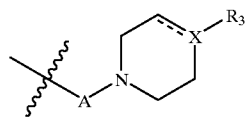

where
A is alkylene of 1 to 4 carbon atoms;
X is a carbon atom, CH, or nitrogen; and
$R_3$ represents either an (un)substituted aryl group selected from phenyl, biphenyl 1,2,3,4-tetrahydronaphthyl, naphthyl, anthryl, or phenanthryl or a (un)substituted heteroaryl group selected from the group consisting of, pyridyl, pyrimidin-2-yl, 1- or benzoisothiazol-3-yl; wherein said (un)substituted aryl or (un)substituted heteroaryl group is substituted with substitutuents independently selected from $C_1$–$C_6$ alkyl, $C_1$–$C_4$ alkoxy, hydroxy, phenyl, amino, mono- or di($C_1$–$C_6$)alkylamino, and trifluoromethyl; and
$R_4$ is hydrogen or $C_1$–$C_6$ alkyl.
2. A compound of the formula:

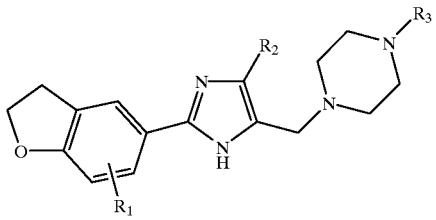

or a pharmaceutically acceptable salt thereof wherein:
$R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, trifluoromethyl or trifluoromethoxy;
$R_2$ represents halogen or $C_1$–$C_6$ alkyl; and
$R_3$ represents either an (un)substituted aryl group selected from phenyl, biphenyl 1,2,3,4-tetrahydronaphthyl, naphthyl, anthryl, or phenanthryl or a (un)substituted heteroaryl group selected from the group consisting of pyridyl, pyrimidin-2-yl, 1-or benzoisothiazol-3-yl;

wherein said (un)substituted aryl or (un)substituted heteroaryl group is substituted with zero to three substitutents independently selected from $C_1$–$C_6$ alkyl, $C_1$–$C_4$ alkoxy, hydroxy, phenyl, amino, mono- or di($C_1$–$C_6$)alkylamino, and trifluoromethyl.

3. A compound of the formula:

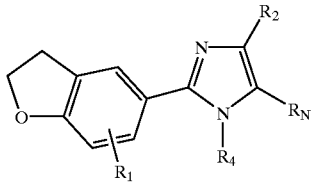

or the pharmaceutically acceptable salts thereof wherein:

$R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$) alkylamino, cyano, nitro, trifluoromethyl or trifluoromethoxy;

$R_2$ represents halogen or $C_1$–$C_6$ alkyl; and $R_N$ is

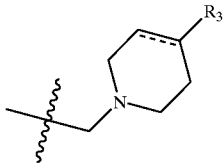

where $R_3$ represents phenyl, pyridyl, pyrimidin-2-yl, 1- or 2-naphthyl, quinolinyl, isoquinolinyl, benzopyrimidinyl or benzoisothiazol-3-yl, each of which is optionally substituted with up to three groups selected form halogen, $C_1$–$C_6$ alkyl, $C_1$–$C_4$ alkoxy, $C_1$–$C_6$ alkylthio, hydroxy, amino, mono- or di($C_1$–$C_6$) alkylamino, phenyl, cyano, nitro, trifluoromethyl or trifluoromethoxy.

4. A compound according to claim 3 wherein $R_N$ is

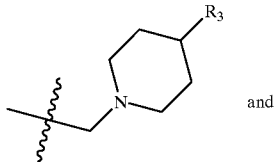

and $R_3$ is pyrimidinyl, phenyl, pyridyl, naphthyl, benzyl, 4,5-benzopyrimidin-2-yl, isoquinoline, each of which $R_3$ groups is optionally unsubstituted or substituted with up to three groups selected from halogen, $C_1$–$C_6$ alkyl, $C_1$–$C_4$ alkoxy, hydroxy, phenyl, amino, mono- or di($C_1$–$C_6$)alkylamino, or trifluoromethyl.

5. A compound according to claim 3, wherein $R_N$ is

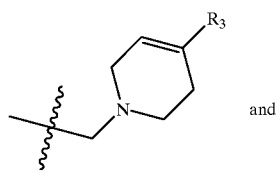

and $R_3$ is pyrimidinyl, phenyl, pyridyl, naphthyl, benzyl, 4,5-benzopyrimidin-2-yl, isoquinoline, each of which $R_3$ group is optionally unsubstituted or substituted with up to three groups selected from halogen, $C_1$–$C_6$ alkyl, $C_1$–$C_4$ alkoxy, hydroxy, phenyl, amino, mono- or di($C_1$–$C_6$)alkylamino, or trifluoromethyl.

6. A compound according to claim 1, which is 2-(2,3-Dihydrobenzofuran-5-yl)-4-(1-[4-{2-methoxyphenyl}piperazin-1-yl]methyl)imidazole.

7. A compound according to claim 1, which is 2-(2,3-Dihydrobenzofuran-5-yl)-4-(1-[4-{pyridin-2-yl}piperazin-1-yl]methyl)imidazole.

8. A compound according to claim 1, which is 2-(2,3-Dihydrobenzofuran-5-yl)-4-(1-[4-{5-methylpyrimidin-2-yl}piperazin-1-yl]methyl)imidazole.

9. A compound according to claim 1, which is 2-(2,3-Dihydrobenzofuran-5-yl)-4-(1-[4-{2-napthyl}piperazin-1-yl]methyl)imidazole.

10. A compound according to claim 1, which is 2-(2,3-Dihydrobenzofuran-5-yl)-4-(1-[4-{4,5-benzopyrimidin-2-yl}piperazin-1-yl]methyl)imidazole.

11. A compound according to claim 1, which is 2-(2,3-Dihydrobenzofuran-5-yl)-4-(1-[4-{isoquinolin-1-yl}piperazin-1-yl]methyl)imidazole.

12. A compound according to claim 1, which is 2-(2,3-Dihydrobenzofuran-5-yl)-4-(1-[4-phenylpiperazin-1-yl]methyl)imidazole.

13. A compound according to claim 1, which is 2-(2,3-Dihydrobenzofuran-5-yl)4-(1-[4-{2-ethoxyphenyl}piperazin-1-yl]methyl)imidazole.

14. A compound according to claim 1, which is 2-(2,3-Dihydrobenzofuran-5-yl)-4-(1-[4-{2-methylphenyl}piperazin-1-yl]methyl)imidazole.

15. A compound according to claim 1, which is 2-(2,3-Dihydrobenzofuran-5-yl)-4-(1-[4-{3-chlorophenyl}piperazin-1-yl]methyl)imidazole.

16. A compound according to claim 1, which is 2-(2,3-Dihydrobenzofuran-5-yl)-4-(1-[4-{4-methoxyphenyl}piperazin-1-yl]methyl)imidazole.

17. A compound according to claim 1, which is 2-(2,3-Dihydrobenzofuran-5-yl)-4-(1-[4-{4-fluorophenyl}piperazin-1-yl]methyl)imidazole.

18. A compound according to claim 1, which is 2-(2,3-Dihydrobenzofuran-5-yl)-4-(1-[4-{2-fluorophenyl}piperazin-1-yl]methyl)imidazole.

19. A compound according to claim 1, which is 2-(2,3-Dihydrobenzofuran-5-yl)-4-(1-[4-{2-chlorophenyl}piperazin-1-yl]methyl)imidazole.

20. A compound according to claim 1, which is 2-(2,3-Dihydrobenzofuran-5-yl)-4-(1-[4-{3-trifluoromethylphenyl}piperazin-1-yl]methyl)imidazole.

21. A compound according to claim 1, which is 2-(2,3-Dihydrobenzofuran-5-yl)-4-(1-[4-{2,3-dimethylphenyl}piperazin-1-yl]methyl)imidazole.

22. A compound according to claim 1, which is 2-(2,3-Dihydrobenzofuran-5-yl)-4-(1-[4-{5-methoxypyrimidin-2-yl}piperazin-1-yl]methyl)imidazole.

23. A compound according to claim 1, which is 2-(2,3-Dihydrobenzofuran-5-yl)-4-(1-[4-{5-fluoropyrimidin-2-yl}piperazin-1-yl]methyl)imidazole.

24. A compound according to claim 1, which is 2-(2,3-Dihydrobenzofuran-5-yl)-4-(1-[4-{pyrimidin-2-yl}piperazin-1-yl]methyl)imidazole.

25. A compound according to claim 1, which is 2-(2,3-Dihydrobenzofuran-5-yl)-4-(1-[4-{5-phenylpyrimidin-2-yl}piperazin-1-yl]methyl)imidazole.

26. A compound according to claim 1, which is 2-(2,3-Dihydrobenzofuran-5-yl)-4-(1-[4-{4-methylpyrimidin-2-yl}piperazin-1-yl]methyl)imidazole.

27. A compound according to claim 1, which is 2-(2,3-Dihydrobenzofuran-5-yl)-4-(1-[4-{4-trifluoromethylpyrimidin-2-yl}piperazin-1-yl]methyl)imidazole.

28. A compound according to claim 1, which is 2-(2,3-Dihydrobenzofuran-5-yl)-4-(1-[4-phenylpiperidin-1-yl]methyl)imidazole.

29. A compound according to claim 1, which is 2-(2,3-Dihydrobenzofuran-5-yl)-4-(1-[4-benzylpiperidin-1-yl]methyl)imidazole.

30. A compound according to claim 1, which is 2-(2,3-Dihydrobenzofuran-5-yl)-4-(1-[4-phenyl-1,2,5,6-tetrahydopyridin-1-yl]methyl)imidazole.

31. A compound of the formula:

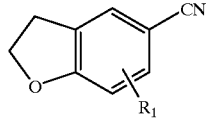

wherein $R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, trifluoromethyl or trifluoromethoxy.

32. A compound of the formula:

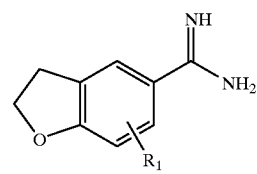

wherein:

$R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, trifluoromethyl or trifluoromethoxy.

33. A compound of the formula:

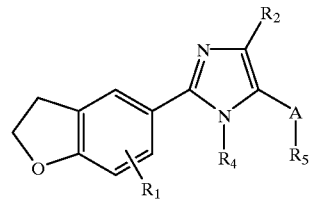

wherein:

A is alkylene of 1 to 4 carbon atoms;
$R_1$ represents hydrogen, halogen, $C_1$–$C_6$ alkyl, $C_1$–$C_4$ alkoxy, $C_1$–$C_6$ alkylthio, hydroxy, amino, mono- or di($C_1$–$C_6$)alkylamino, cyano, nitro, trifluoromethyl or trifluoromethoxy;
$R_2$ represents halogen or $C_1$–$C_6$ alkyl;
$R_5$ is hydroxy or halogen; and
$R_4$ is hydrogen or $C_1$–$C_6$ alkyl.

34. A method for the treatment of schizophrenia, mania, depression, anxiety, compulsive behavior, or Parkinson-like motor disorders comprising admistering to a patient in need of such treatment an effective amount of a compound or pharmaceutically acceptable salt of claim 1.

35. A pharmaceutical composition comprising a compound or salt according to claim 1 and a pharmaceutically acceptable carrier.

* * * * *